United States Patent
Doguet et al.

(10) Patent No.: US 11,883,196 B2
(45) Date of Patent: Jan. 30, 2024

(54) ACTIVE IMPLANTABLE STIMULATING DEVICE FOR ON-DEMAND STIMULATION OF A VAGUS NERVE

(71) Applicant: Synergia Medical, Mont-Saint-Guibert (BE)

(72) Inventors: Pascal Doguet, Mont-Saint-Guibert (BE); Jérôme Garnier, Mont-Saint-Guibert (BE); Jean Delbeke, Mont-Saint-Guibert (BE)

(73) Assignee: Synergia Medical, Mont-Saint-Guibert (BE)

( * ) Notice: Subject to any disclaimer, the term of this patent is extended or adjusted under 35 U.S.C. 154(b) by 0 days.

(21) Appl. No.: 17/791,728

(22) PCT Filed: Jan. 9, 2020

(86) PCT No.: PCT/EP2020/050379
§ 371 (c)(1),
(2) Date: Jul. 8, 2022

(87) PCT Pub. No.: WO2021/139887
PCT Pub. Date: Jul. 15, 2021

(65) Prior Publication Data
US 2023/0038649 A1     Feb. 9, 2023

(51) Int. Cl.
*A61N 1/36*      (2006.01)
*A61B 5/00*      (2006.01)
(Continued)

(52) U.S. Cl.
CPC ............ *A61B 5/6803* (2013.01); *A61B 5/369* (2021.01); *A61N 1/36053* (2013.01);
(Continued)

(58) Field of Classification Search
CPC ......... A61B 5/6803; A61B 5/369; A61B 5/31; A61B 5/7405; A61B 5/37; A61B 5/372;
(Continued)

(56) References Cited

U.S. PATENT DOCUMENTS 4,702,254 A   10/1987  Zabara
5,215,086 A *  6/1993  Terry, Jr. ............ A61N 1/36053
                                                     607/46
(Continued)

FOREIGN PATENT DOCUMENTS

WO     2019042553 A1    3/2019

OTHER PUBLICATIONS

Int'l Search Report for PCT/EP2020/050379, dated Sep. 11, 2020.

*Primary Examiner* — Eugene T Wu
(74) *Attorney, Agent, or Firm* — MaxGoLaw PLLC

(57) ABSTRACT

An active implantable stimulating device (10) includes:
(a) a tissue coupling unit (40) for being implanted directly onto a vagus nerve (Vn) of a patient,
(b) an EEG-unit (70) for measuring an electroencephalogram of the patient,
(c) an encapsulation unit (50) configured for being subcutaneously implanted,
(d) an energy transfer lead (30) for transferring pulses of electrical and/or optical energy,
(e) a signal transfer lead (60) for transferring signals between the EEG unit and the encapsulation unit. EEG electrodes (70a-70d) monitor the electric activity of the brain of a patient. The EEG signal is conveyed to the electronic circuit (53) in the form of EEG conditioned data. The electronic circuit analyses the EEG conditioned data to yield analysis results. The electronic circuit takes a decision to trigger energy pulses to stimulate the vagus nerve (VN).

13 Claims, 4 Drawing Sheets

(51) Int. Cl.
*A61B 5/369* (2021.01)
*A61B 5/31* (2021.01)

(52) U.S. Cl.
CPC ..... *A61N 1/36064* (2013.01); *A61N 1/36125* (2013.01); *A61B 5/31* (2021.01); *A61B 5/7405* (2013.01)

(58) Field of Classification Search
CPC ..... A61B 5/383; A61B 5/4076; A61B 5/4836; A61N 1/36053; A61N 1/36064; A61N 1/36125; A61N 1/0556; A61N 1/36071; A61N 1/3787; A61N 5/0622; A61N 1/36067; A61N 1/36135; A61N 1/36167
See application file for complete search history.

(56) References Cited

U.S. PATENT DOCUMENTS

| | | | |
|---|---|---|---|
| 6,016,449 A * | 1/2000 | Fischell | G16H 20/40 607/45 |
| 2003/0004428 A1 | 1/2003 | Pless et al. | |
| 2007/0100378 A1 * | 5/2007 | Maschino | A61N 1/32 607/2 |
| 2016/0310070 A1 | 10/2016 | Sabesan | |
| 2017/0368358 A1 * | 12/2017 | Doguet | A61N 1/3787 |

* cited by examiner

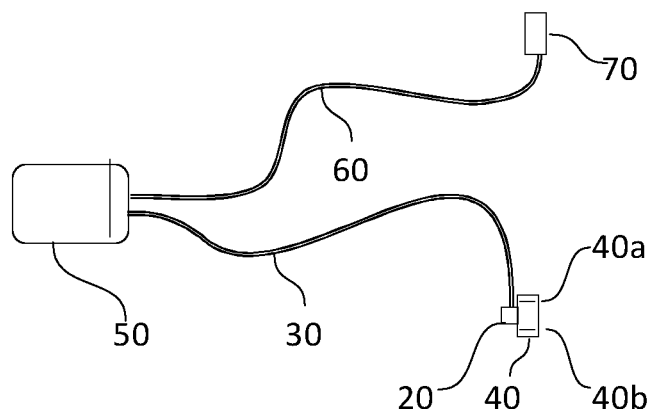
FIG.1
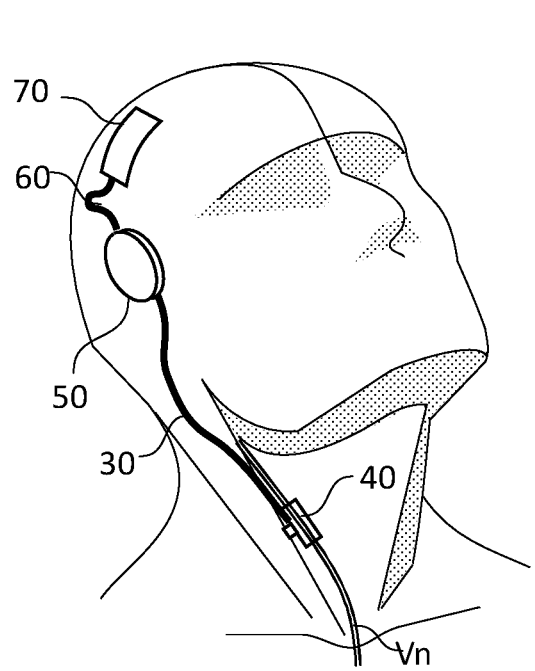 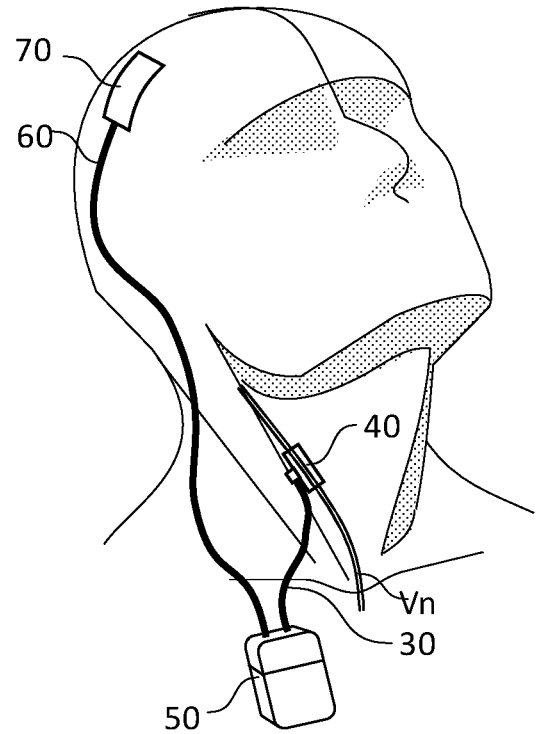
FIG.2(a)  FIG.2(b)

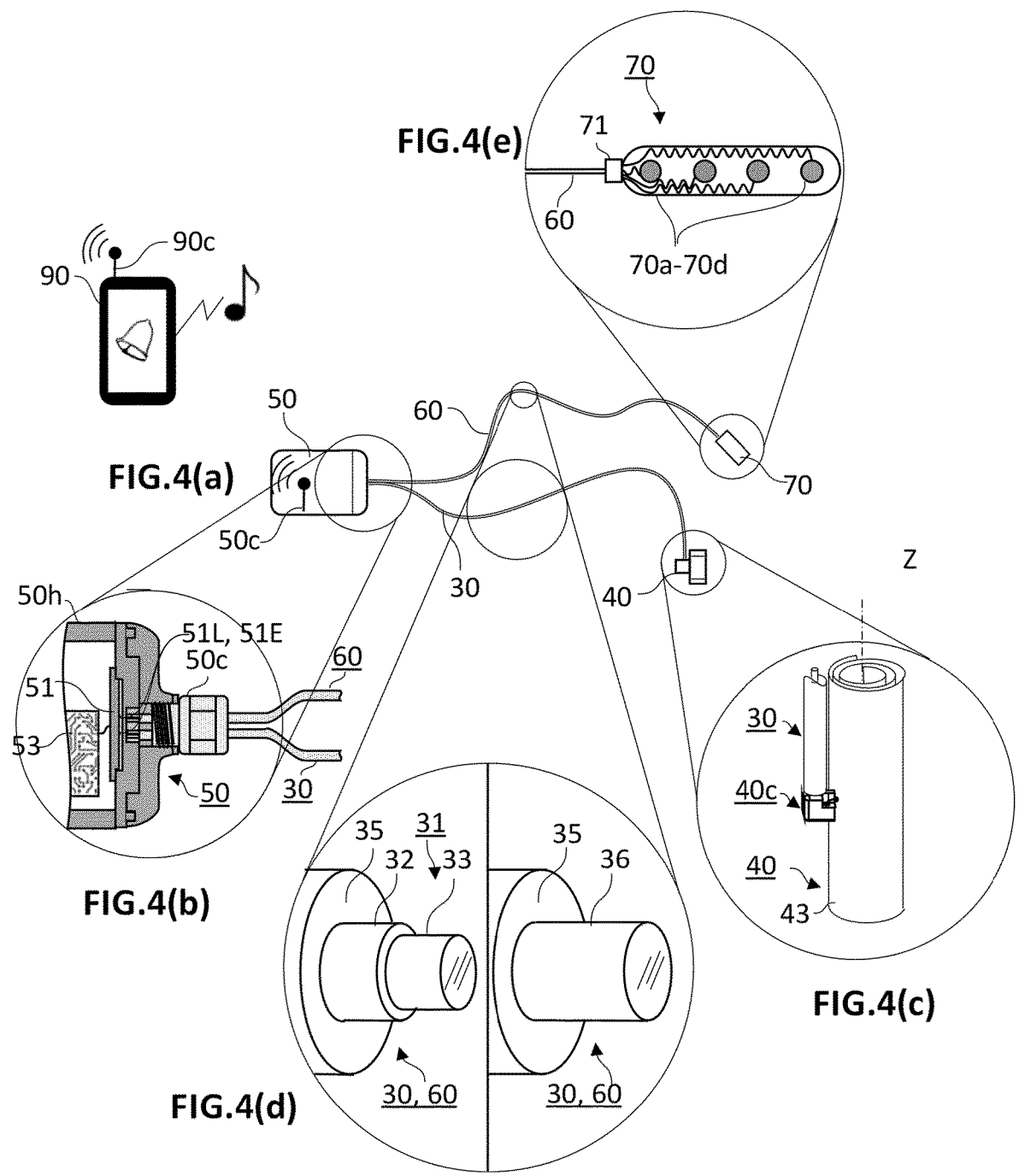

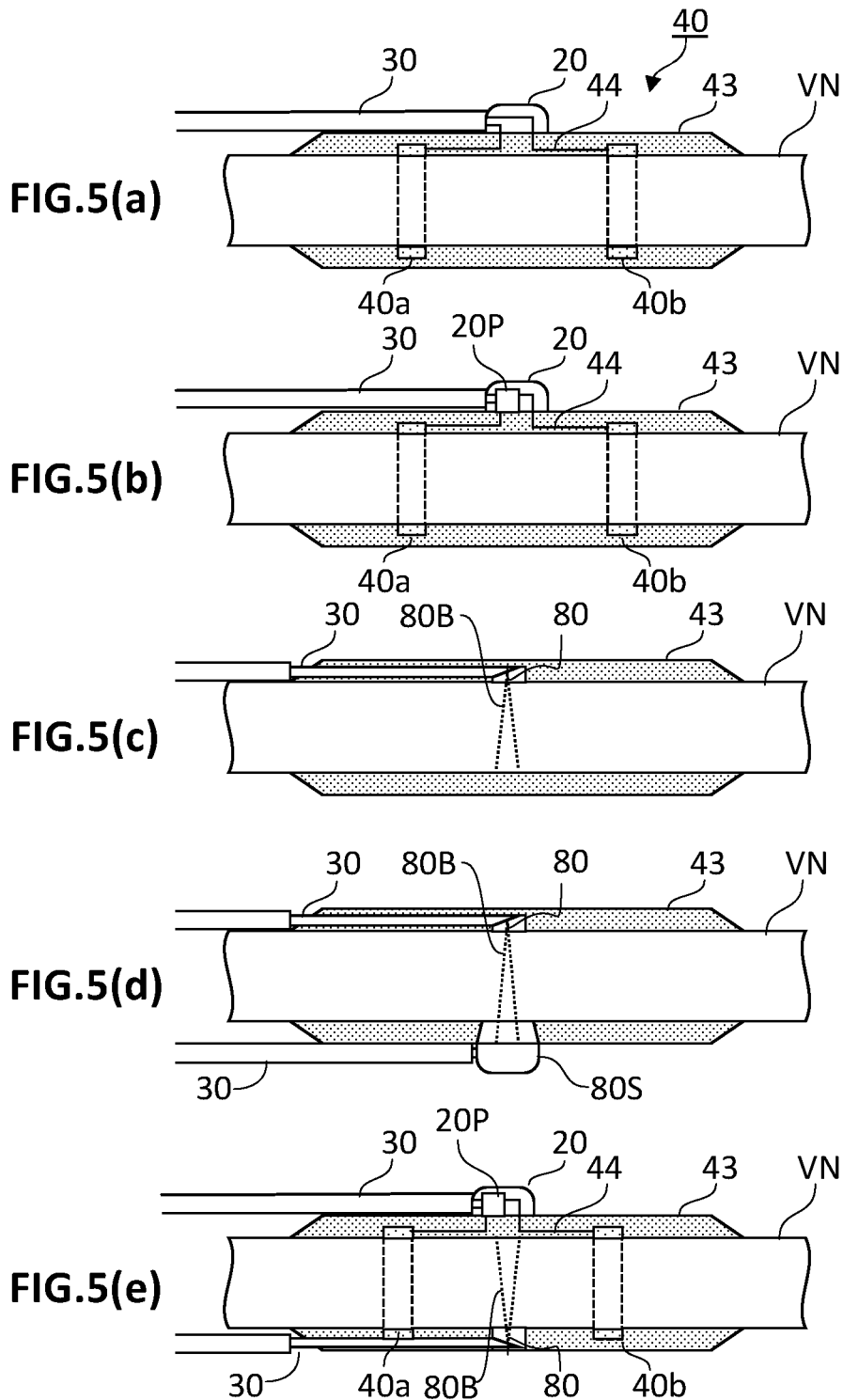

ACTIVE IMPLANTABLE STIMULATING DEVICE FOR ON-DEMAND STIMULATION OF A VAGUS NERVE

TECHNICAL FIELD

The present invention is in the field of electronic active implantable medical devices (AIMD) for use in medical treatments involving the controlled transmission of energy pulses between an implanted pulse generator (IPG) enclosed in an encapsulation unit and a tissue coupling unit coupled to a target tissue such as the vagus nerve of a patient by transmission of energy through conductive wires or optical fibres between the IPG and the tissue coupling unit. The emission of energy pulses by the IPG is conditioned by the occurrence of electroencephalogram profiles representative of an imminent or incipient seizure as detected by an electronic circuit enclosed in the encapsulation.

The present invention has the advantage that the IPG does not continuously emit energy pulses at regular intervals so that, on the one hand, power is saved thus prolonging the service life of a battery, or the service time between two loading operations of a rechargeable battery and, on the other hand, habituation to the stimulation pulses or desensitization of a target tissue does not occur easily in the patient.

BACKGROUND OF THE INVENTION

Active implantable medical devices (AIMD) have been used for decades for treating a number of disorders, in particular neurological disorders. A major type of AIMD's consists of neurostimulators, which deliver electrical pulses to a tissue such as a nerve or a muscle for diagnosing or treating a number of disorders such as Parkinson's disease, epilepsy, chronic pain, motor disorders, and many other applications. Depending on the tissue to be treated, the type of electrodes used, and the distance between electrodes, the voltage required between implanted electrodes can be of the order of 15V±5V. Such voltage requires an implanted pulse generator (IPG) and a source of electric power (such as a battery) of such dimensions that electric stimulating implants are generally formed of two separate components: on the one hand, the electrodes which are implanted directly onto the tissue to be treated and, on the other hand, the implanted pulse generator and battery, of larger dimensions, and enclosed in an encapsulation unit, which can be implanted at various locations in the body depending upon the application but most often in the subclavian region, the lower abdominal area or gluteal region. The energy pulses are transferred from the IPG to the tissue coupling unit via an energy transfer lead, which can be formed of conductive wires or optical fibres coupled to a photovoltaic cell for transforming optical energy into electrical energy, as described, e.g., in EP3113838B1. In case of conductive wires, the IPG emits electric pulses, and in case of optical fibres, the IPG emits optical pulses.

In recent years, treatment of tissues with optical energy has shown encouraging potential for the treatment of disorders, either to support the field of optogenetics or using the direct effect of infrared or other wavelengths of light. For such light treatments of a tissue, a so-called optrode can be used. An optrode can be a light emitter focusing a light beam onto a precise area of a tissue, or it can be a light sensor, sensing a reflected, transmitted, or scattered light beam emitted by a light emitter.

The IPG's in neurostimulators are generally configured for continuously emitting trains of pulses of given frequencies, durations, and intensities separated from one another by predefined intervals, during the whole period of the treatment, which can last years. This has two downsides. First, it consumes a lot of energy and even if rechargeable batteries are used, the service time of a battery between two successive re-charging operations can become quite short, thus increasing the frequency of such re-charging operations, which are quite cumbersome and uncomfortable for the patient. Second, the repetitive stimulations of a nerve can develop a habituation of the body of the patient to said stimulations, which reduces the curative effect correspondingly. To date, however, this is a reality of neurostimulators available on the market, and one must live with it.

Prediction of seizures in patients suffering from illnesses like epilepsy or Parkinson has been the subject of numerous studies. For example, magnetic resonance imaging (MRI) and 5 electroencephalographic measurements in the form of an electroencephalogram (EEG) have been used to predict such seizures minutes before they actually happened, or at least at a very early stage of a seizure. Electroencephalography is an electrophysiological monitoring method to record electrical activity of the brain. EEG can be measured with an array of extracranial electrodes or with intracranial electrodes. FIG. 3 shows an example of EEG with a period (1) of normal cerebral activity, followed by a period (3) of seizure separated from the former period by a transition period (2) representative of features announcing the coming occurrence of a seizure.

The company Neuropace developed a responsive neurostimulation (RNS) device for treating drug-resistant focal epilepsy treatment by cortical electrical stimulations triggered by seizure detection algorithms that run on-board a standard micro-controller within the device. Focal epilepsy is a specific type of epilepsy which is diagnosed when the source of epilepsy is focalized in one area of the brain.

The foregoing RNS device is highly invasive, requiring boring through the skull and placing electrodes into the brain. Furthermore, it only works for treatment of focal epilepsy, as monitoring of the EEG and stimulation both occur in a precisely delimited area of the brain.

Therefore, there remains a need for on-demand stimulation devices, responsive to a signal indicative of a coming, incipient, or ongoing seizure which is not restricted to focal epileptic seizures, and which combine low invasiveness, reliable sensing of EEG for predicting upcoming seizures or detecting incipient seizures, and very low power consumption. The present invention proposes such a device that combines all the foregoing properties and more advantages as described in continuation;

SUMMARY OF THE INVENTION

The present invention is defined in the appended independent claims. Preferred embodiments are defined in the dependent claims. In particular, the present invention concerns an implantable stimulating device for electrically or optically stimulating a vagus nerve, comprising, (a) a tissue coupling unit comprising one or more electrodes or optrodes configured for being implanted directly onto the vagus nerve of a patient, (b) an EEG-unit configured for measuring an electroencephalogram (EEG-) signal of the patient, (c) an encapsulation unit configured for being subcutaneously implanted in the patient body, and comprising a housing) enclosing, an implanted pulse generator (IPG) configured for emitting pulses of electrical or optical energy, an electronic circuit configured for sending a triggering signal to the IPG instructing the IPG to trigger energy pulses, (d) an energy transfer lead including one or more electric wires and/or optical fibres, configured for transferring pulses of electrical and/or optical energy between the IPG and the tissue coupling unit, and comprising a proximal end configured for coupling to the encapsulation unit and a distal end configured for coupling to the tissue coupling unit, (e) a signal transfer lead including one or more electric wires and/or optical fibres, configured for transferring signals between the EEG-unit and the electronic circuit, and comprising a proximal end configured for coupling to the encapsulation unit and a distal end configured for coupling to the EEG-unit, wherein the electronic circuit is configured for, receiving EEG-conditioned data from the signal transfer lead (60), which is representative of the EEG signal measured by the EEG-unit, and carrying out an analysis of the EEG-conditioned data yielding analysis results and taking a decision based on the analysis results and controlling the IPG according to the decision, wherein the decision includes instructing the IPG to send one or more energy pulses if the analysis results are representative of either a coming seizure, or an incipient or ongoing seizure, The step of controlling the IPG includes after instructing the IPG to send one or more pulses, to instruct the IPG to keep sending pulses either, until the analysis results become indicative of an end of a seizure, or for a predetermined duration in time, and thereafter to stop sending pulses until the analysis results are again representative of either a coming seizure, or an incipient or ongoing seizure.

The energy pulses can be optical pulses or electric pulses. For optical pulses, the IPG can comprise one or more light sources, the energy transfer lead can comprise one or more optical fibres in optical communication with the one or more light sources of the IPG, and the tissue coupling unit can comprise one or more photovoltaic cells in optical communication with one or more of the optical fibres and in electrical communication with the one or more electrodes.

For electrical pulses, the IPG can comprise an electric pulse generator and the energy transfer lead can comprise one or more electric wires in electrical contact with the electric pulse generator and with the one or more electrodes of the tissue coupling unit.

The EEG-conditioned data can be transferred from the EEG-unit to the encapsulation unit in the form of optical signals or electric signals. For optical signals, the EEG-unit can comprise an EEG-conditioning circuit configured for conditioning the EEG-signal to yield the EEG-conditioned data, the EEG-conditioning circuit comprising one or more light sources configured for emitting a light signal representative of the EEG-signal measured by the EEG-electrodes (70a-70d) and forming the EEG-conditioned data, the signal transfer lead (60) can comprise one or more optical fibres in optical communication with one or more light sources of the EEG-conditioning circuit and the encapsulation unit can comprise one or more photodetectors in optical communication with the one or more optical fibres of the signal transfer lead, the photodetectors being in communication with the electronic circuit.

For electrical signals, the EEG-unit can comprise an EEG-conditioning circuit (71C) configured for conditioning the EEG-signal to yield the EEG-conditioned data, and preferably comprises an electric socket in conductive contact with the EEG-conditioning circuit, the signal transfer lead can comprise one or more conductive wires each comprising a proximal end and a distal end, wherein the distal ends of the one or more conductive wires can be coupled in conductive contact with the EEG-conditioning circuit, preferably through the electric socket and the proximal ends of the one or more conductive wires can be in conductive contact with the electronic circuit of the encapsulation unit.

For both optical and electrical signals, the EEG-conditioning circuit can comprise one or more of the following elements, one or more amplifiers to yield an amplified EEG-signal, filters for filtering the amplified EEG-signal and yielding a filtered EEG-signal, an analog-to-digital (A/D) converter for digitizing the amplified EEG-signal or the filtered EEG-signal to yield a digitized EEG-signal, An encoding and signal compressing and multiplexing logic to reduce size of the data to be transmitted, and a driver for modulating and/or driving the thus treated EEG-signal through the signal transfer lead.

In order to energize the EEG-circuit, the signal transfer lead preferably comprises an optical fibre with a proximal end in optical communication with a light source enclosed in the housing, and with a distal end in optical communication with a photovoltaic cell configured for transforming optical energy into electric energy in electrical contact with the EEG-conditioning circuit for energizing the EEG-conditioning circuit.

In the present invention, it is preferred that both energy transfer lead and signal transfer lead comprise no electric wire.

The EEG-unit comprises EEG-electrodes configured for measuring the electrical activity of an area of the brain. The EEG-electrodes can be selected among one or more of, subcutaneous electrodes configured for being implanted subcutaneously over the skull, preferably attached to the skull, or epidural electrodes configured for being implanted epidurally, namely under the skull and over the dura mater, or brain electrodes configured for being implanted below the dura matter and directly over the brain surface, or intra-cerebral electrodes, configured for being implanted within the brain.

In a preferred embodiment, the encapsulation comprises no battery, and comprises a coil for inducing an electric current upon exposure to a magnetic field from an external source of energy, in a similar fashion as used with cochlear implants. This embodiment allows the size of the housing to be reduced substantially.

Alternatively, the encapsulation can enclose a battery for energizing the implantable stimulating device, wherein the battery is preferably a rechargeable battery.

BRIEF DESCRIPTION OF THE FIGURES

For a fuller understanding of the nature of the present invention, reference is made to the following detailed description taken in conjunction with the accompanying drawings in which:

FIG. 1: shows an AIMD according to the present invention.

FIG. 2: shows two embodiments of AIMD's according to the present invention, (a) with an encapsulation implanted at the level of an ear, as is used with cochlear implants, and (b) with the encapsulation implanted in a subclavian region.

FIG. 4: shows an AIMD according to the present invention, including (a) an overall view, (b) an example of an encapsulation unit (c) an example of a tissue coupling unit, (d) examples of energy and signal transfer leads, and (e) an example of an EEG-unit (70).

FIG. 5: shows various configurations of tissue coupling units (40), (a) cuff electrode, (b) cuff electrode with electrical sensing, (c) cuff optrode with bevelled optical fibre, (d) cuff optrode with optical sensing, (e) optrode with electrical sensing.

DETAILED DESCRIPTION OF THE INVENTION

Figure 3:
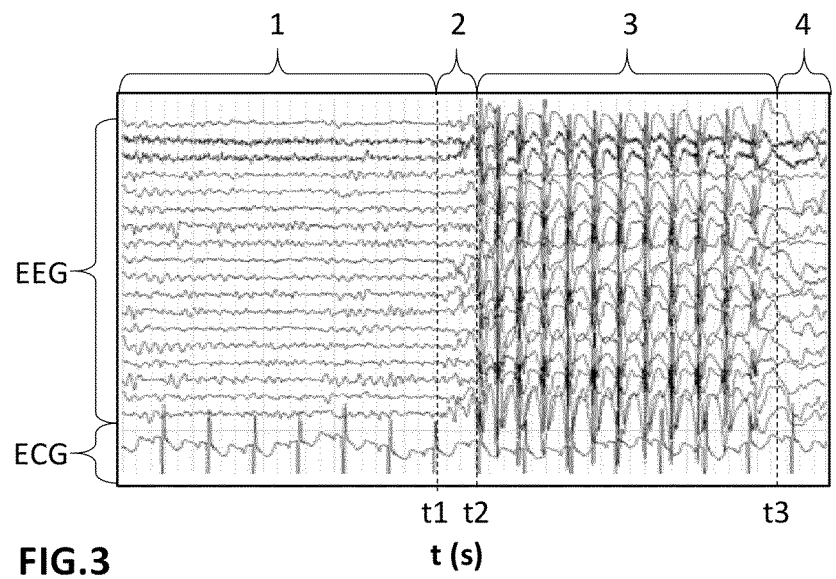
FIG. 3: shows an example of EEG showing (1) a period of normal cerebral activity, (2) a transition period preceding a seizure, (3) a period of seizure, and (4) a recovery period.

As illustrated in FIG. 1, an implantable electrically stimulating device (10) according to the present invention comprises,
  (a) a tissue coupling unit (40) comprising one or more electrodes (40a, 40b) suitable for being implanted directly onto a vagus nerve (Vn) of a patient,
  (b) an EEG-unit (70) configured for measuring an electroencephalogram of the patient,
  (c) an encapsulation unit (50) configured for being subcutaneously implanted in the patient body, and enclosing an implanted pulse generator (IPG) (51) and an electronic circuit (53),
  (d) an energy transfer lead (30) configured for transferring pulses of electrical and/or optical energy between the encapsulation unit and the tissue coupling unit,
  (e) a signal transfer lead (60) configured for transferring signals between the EEG-unit and the encapsulation unit.

Encapsulation Unit (50)

As illustrated in FIGS. 4(a) and 4(b), an optoelectronic active implantable medical device (AIMD's) according to the present invention comprises an encapsulation unit (50) configured for being subcutaneously implanted in the patient body, at a location remote from the vagus nerve to be stimulated. The encapsulation comprises a housing (50h) enclosing,
  an implanted pulse generator (IPG) (51) configured for emitting pulses of electrical or optical energy, and
  an electronic circuit (53) configured for sending a triggering signal to the IPG (51) instructing the IPG to trigger energy pulses.

As partially shown in FIG. 4(b), the housing (50h) of the encapsulation unit (50) defines an inner space enclosing the IPG (51) and the electronic circuit (53). The housing (50h) must be made of a biocompatible material which ensures a tight barrier between the inner space and an environment surrounding the encapsulation after implantation in the patient's body. Housings are often made of metal, such as titanium. Alternatively, the housing can be made of a ceramic material, preferably a ceramic material which is transparent to selected ranges of wavelengths, preferably comprised between 380 and 1800 nm. For example, fused silica can be used for forming the housing (50h) as described in PCT/EP2019/069087. A transparent housing (50h) is advantageous when using an optical IPG (51) as discussed below, and/or when communicating with an exterior of the housing by means of optical signals. A key issue is the long-term moisture tightness of the housing, in particular at the level of welding lines joining different components of the housing or surrounding feedthroughs. Solutions exist in the art, and the present invention is not restricted to any of them.

The IPG can comprise an electric pulse generator (51E) as traditionally used in neurostimulators, such as described e.g., in U.S. Pat. No. 7,720,538. The electrical IPG (51E) enclosed in the housing is brought into conductive contact by means of feedthroughs with one or more conductive wires (36) outside the housing (50h), forming part of the energy transfer lead (30). Feedthroughs are electrical contacts extending through a wall of the housing (not shown).

Alternatively, the IPG (51) can comprise one or more optical components including one or more sources of light emission (51L), light sensors, micro-optics components (e.g., lenses), The source of light emission can emit light pulses at least at a wavelength comprised between 380 and 1800 nm, preferably between 600 and 1500 nm, more preferably between 700 and 900 nm. An example of encapsulation unit suitable for the present invention and comprising an optical IPG (51) is described in WO2018068807. The optical energy pulses generated by the optical IPG located inside the housing are transferred to an optical fibre (31) forming part of the energy transfer lead (30) through a window transparent to the wavelengths emitted by the optical IPG.

The encapsulation unit comprises one or more connection devices (50x) for connecting the encapsulation unit to the energy transfer lead (30) and to the signal transfer lead (60). In case the energy and/or signal transfer leads (30, 60) comprise conductive wires (36), the one or more connection devices (50x) comprise feedthroughs, well known in the art such as in U.S. Pat. No. 7,720,538 cited supra. In case the energy and/or signal transfer leads (30, 60) comprise optical fibres (31), the one or more connection devices comprise one or more windows, transparent to the wavelengths of the light beams transported by the energy and/or signal transfer leads (30, 60). Examples of connection devices (50x) for optical fibres are described e.g., in WO2018068807.

The electronic circuit (53) is discussed in more detail below. The electronic circuit can be an analogue and/or digital circuit and is configured for instructing the IPG (51) to trigger electrical and/or optical energy pulses. It is also configured for processing information received from the EEG-unit (70) or from the tissue coupling unit (40), or from an external processing unit (90) located outside the body of the patient.

In many applications, the encapsulation unit encloses a battery, preferably a rechargeable battery. In case of rechargeable batteries an induction coil is preferably provided either within or outside the inner volume of the housing. Alternatively, an implant devoid of a battery can be energized by an external source of energy located outside the body of the patient, by means of an induction coil. This is used for example with cochlear implants. The encapsulation unit can also include communication means with the external processing unit (90).

Tissue Coupling Unit (40)

As illustrated in FIGS. 5(a), 5(b), and 5(e), the tissue coupling unit (40) can comprise electrodes (40a, 40b) coupled to an insulating support (43), configured for being coupled to a nerve such as the vagus nerve (VN) in contact with the electrodes. For example, the tissue coupling unit (40) can be in the shape of, but is not restricted to, a cuff or helical electrode to be wrapped around the vagus nerve (cf. e.g., WO2019042553 and PCT/EP2018/082703). The insulating support comprises a nerve coupling surface, which may contact the vagus nerve to be treated without causing any neural stimulating effect. The insulating support is used for securing the electrodes at their treatment positions for long term implantation, and for reducing stray currents. The insulating support (43) is preferably made of a polymeric material. If the insulating material must be deformed for insertion and for accommodating any body movement, such as with self-sizing cuff electrodes, it is preferably made of an elastomeric polymer, such as silicone or a polyurethane elastomer, or can be made of a sheet of polyimide. For other electrode geometries, such as slit cuff electrodes, the insulating support can be rigid and made for example of polyurethane or of an epoxy resin.

The resistance of the tissue is of the order of 3-5 kΩ. With a current of the order of 0.1 to 3 mA, the voltage required between electrodes can be of the order of 10 V. The energy transfer lead (30) is coupled to the tissue coupling unit by means of a nerve-connection unit (20). If the energy transfer lead (30) comprises a conductive wire (36), the nerve-connection unit (20) ensures there is a conductive contact between the conductive wire (36) and nerve-connection wires (44) coupled to the electrodes (40a, 40b). If the energy transfer lead (30) comprises an optical fibre (31), the nerve-connection unit (20) includes a photovoltaic cell (20P) between the energy transfer lead (30) and the nerve-connection wires (44) for transforming optical energy into electrical energy, which is conducted to the electrodes (40a, 40b) by the nerve-connection wires (44).

As illustrated in FIGS. 5(c) to 5(e), instead of, or additionally to electrode contacts (40a, 40b), the insulating support sheet (43) can be provided with one or more optical contacts, also called optrodes (80). An optical contact as defined herein can be either a light emitter or a light sensor, or both. In some applications, stimulation of a tissue by light emission is mainly due to localized heating of the tissue. For such applications, it is preferred that the light directed by the optical contact be in the infrared range, preferably in the range of 750 to 3000 nm, more preferably of 1200 to 1800 nm. The cuff optrode suitable for the present invention, however, can be used with light beams (80B) of any wavelength.

An optical contact or optrode (80) can be the end of an optical fibre, which is either bevelled or coupled to a lens, mirror, or other micro-optic device for directing and focusing a light beam (80B) towards a precise area of the tissue to be treated. The optrode can be optically coupled to an optical fibre (31) of an optical energy transfer lead (30), and to an optical IPG (51) housed in the encapsulation unit (50). Alternatively, a light emitting device located on an outer surface of the cuff can be electrically powered by the IPG (51) located in the housing, and the optrode can be coupled to said light emitting device for guiding the light towards the tissue.

The optrode (80) can also include a LED, a VCSEL or other laser diode which is mounted on the insulating sheet such as to be in direct optical contact with the tissue around which the cuff is wrapped. If the insulating sheet is transparent to the light wavelength emitted by the optrode, then the light can be transmitted through the thickness of insulating sheet separating the optical contact from the inner surface of the insulating sheet. If the insulating sheet is not transparent enough for an efficient transmission of the light energy, then a window can be provided at the inner surface of the insulating sheet to expose the optical contact.

As illustrated in FIG. 5(d), the tissue coupling unit (40) can further comprise a light sensing unit (80S) for sensing the light scattered, reflected or transmitted after interaction of the beam (80B) with the tissue. The optical signal thus sensed can be transmitted to the electronic circuit (53) in the housing, either in the form of light through a second optical fibre, or of a second electric signal through a conductive wire, provided the light sensing unit is capable of transforming a light signal into an electric signal (e.g., with a photovoltaic cell). The optical signal can be conditioned prior to being transferred through the signal transfer lead, as is described in continuation with respect to the EEG-conditioning circuit (71c).

Energy Transfer Lead (30)

The energy transfer lead (30) is used to transfer energy from the encapsulation (1) to the tissue coupling unit (50) and back. The energy can be in the form of electrical energy. In this case, the energy transfer lead (30) comprises at least one conductive wire (36) as shown in FIG. 4(d), right-hand half circle. If the energy is optical energy, the energy transfer lead (30) comprises at least one optical fibre (31) as shown in FIG. 4(d), left-hand half circle. The optical fibre (31) comprises a core (33) and a cladding (32) surrounding the core and forcing a light beam to propagate within the core. In some instances, a coating is applied over the cladding (not shown). Optical fibres often comprise a glass core (33), but for use in AIMD's, the use of polymer optical fibres (POF) is preferred, for safety reasons. Examples of POF's suitable for use in an AIMD according to the present invention are described in PCT/EP2019/071803. The energy transfer lead (30) can comprise more than one conductive wire and/or optical fibre, either to transfer different forms of energies (e.g., light beams of different wavelengths), or for transferring signals between the tissue coupling unit (40) and the encapsulation unit (50). For example, the tissue coupling unit (40) can send an electrical or optical signal to the electronic circuit (53) of the encapsulation indicative that an electric pulse had reached the electrodes of the tissue coupling unit (40).

In a preferred embodiment, the IPG comprises more than one light source and/or photosensors, and the energy transfer lead (30) includes more than one optical fibre for adding functionalities to the AIMD. For example, an optical fibre (31) can be used for transferring optical energy pulses from the optical IPG to a photovoltaic cell (20P) included in the nerve-connection unit (20) of the tissue coupling unit (50). A second optical fibre can be used to send a feedback signal from a light source included in the tissue coupling unit (40) to a photodetector in the encapsulation housing, which feedback signal can be indicative that an electric pulse has been delivered to the vagus nerve. A third optical fibre can be used to activate a recovery circuit in the tissue coupling unit, to prevent damaging side effects. The third optical fibre can transfer optical energy from a recovering source of light emission lodged in the encapsulation housing to a recovery photovoltaic cell to electrically feed the electrodes, thus forming an electrical charge recovering circuit in parallel with the electrical stimulating circuit. A tissue coupling unit comprising a recovery circuit is described e.g., in WO2016131492.

The energy transfer lead (30) preferably comprises a protective tubing (35) to protect the conductive wire(s) and/or optical fibre(s) from moisture and mechanical rupture. If the energy transfer lead (30) comprises more than one conductive wires and/or optical fibres, these are advantageously enclosed in a single protective tubing (35).

The energy transfer lead (30) comprises a proximal end configured for coupling to the connection device (50x) of the encapsulation unit and a distal end configured for coupling to the nerve-connection unit (20) of the tissue coupling unit (40).

EEG-Unit (70)

Figure 6A:
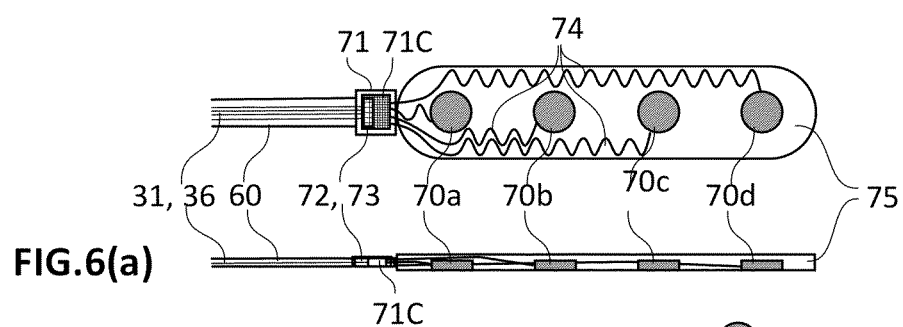
FIG. 6: Shows two embodiments (a) and (b) of EEG-electrode geometries, and (c) representation of an EEG-conditioning circuit.
Figure 6B:
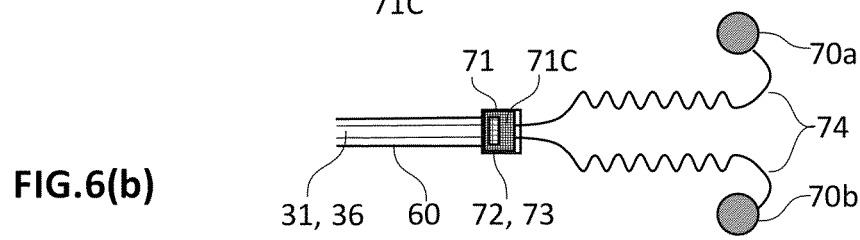

As shown in FIGS. 6(a) and 6(b), the EEG-unit (70) comprises EEG-electrodes (70a-70d) configured for measuring the electric activity of an area of the brain. The electrodes can be selected among one or more of, subcutaneous electrodes configured for being implanted subcutaneously over the skull, preferably attached to the skull, or epidural electrodes configured for being implanted epidurally, namely under the skull and over the dura mater, or brain electrodes configured for being implanted below the dura matter and directly over the brain surface, or intra-cerebral electrodes, configured for being implanted within the brain.

The electrodes can also be applied directly onto the skin of the head of the patient (=extracranial), but to enhance the signal to noise ratio they are preferably implanted subcutaneously. In order to minimize invasiveness of the device, the electrodes are preferably subcutaneous electrodes or epidural electrodes as defined supra. In extreme cases, electrodes can be implanted through a skull opening onto the cortex surface or into the brain, but if not necessary for therapeutic reasons, it is preferred to avoid such invasive configuration. For the patient comfort, and a good signal to noise ratio.

The EEG-electrodes measure a potential difference between a target electrode and a reference electrode. In a preferred embodiment, at least two EEG-electrodes (70a-70d) are mounted on a flexible EEG-support (75) as shown in FIG. 6(a). The EEG-support can be in the form of a thin strip, which is very thin and made of an insulative material, such as a polymer such as a polyimide film, preferably an elastomer, such as a silicone. The EEG-support can carry an array of several EEG-electrodes (70a-70d). EEG-electrodes mounted on a flexible EEG-support of various geometries and configurations suitable for being implanted subcutaneously are available on the market.

In an alternative embodiment, at least two EEG-electrodes can be freely implanted at different locations of the skull as illustrated in FIG. 6(b). This embodiment gives more freedom for optimizing the positioning of the EEG-electrodes without limitation by their being mounted on an EEG-support (75).

The present invention is suitable for treating all types of epilepsies as well as other diseases and, unlike the responsive neurostimulation (RNS) device developed by Neuropace, is not limited to focal epilepsy. The optimal number and positioning of the EEG-electrodes (70a-70d) over the skull can be determined by separate clinical EEG-measurements of the electric activity of the brain during an extended duration. Such clinical measurements are generally carried out with the patient wearing a "helmet" during the whole duration of the clinical tests, which supports a full array of electrodes covering a whole area of the patient's cranium. These clinical measurements allow identifying the areas of the brain between two or more measuring electrodes yielding the most pertinent or appropriate signals indicative of a coming seizure. The results of the clinical measurements are used to determine the best positioning and number of EEG-electrodes (70a-70d) to be implanted subcutaneously. The EEG-signal measured by the EEG-electrodes can be too weak and too noisy for being transferred as such through the signal transfer lead (60) to the encapsulation unit, for the electronic circuit (53) to draw any conclusive and reliable information of a coming or incipient seizure. For increasing the level of confidence of the analysis carried out by the electronic circuit (53) it is preferred to treat the EEG-signal measured by the EEG-electrodes prior to transferring it through the signal transfer lead (60), by conditioning it by means of an EEG-conditioning circuit (71C).

EEG-Conditioning Circuit (71C)

Figure 6C:
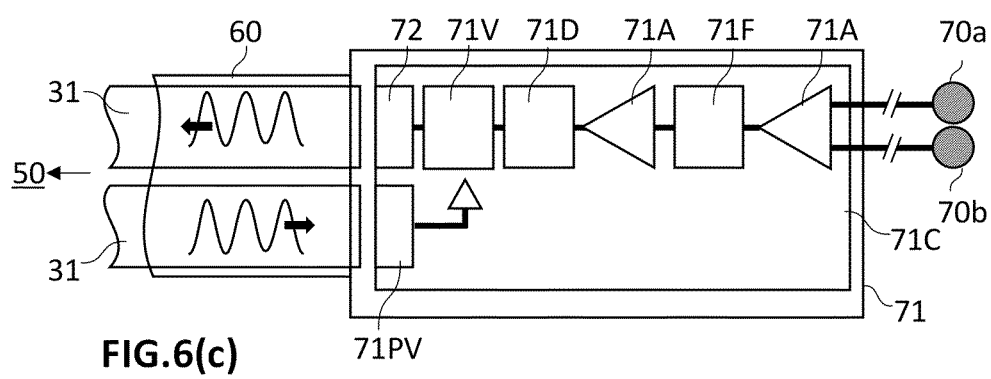

As illustrated in FIG. 6(c), an EEG-conditioning circuit (71C) is preferably positioned between the EEG-electrodes (70a-70d) and the signal transfer lead (60). The EEG-conditioning circuit (71C) is configured for conditioning the EEG-signal to yield the EEG-conditioned data, and is preferably housed in a EEG-connection unit (71).

As illustrated in FIG. 6(c), the EEG-conditioning circuit can comprise a first stage of preamplification with an amplifier (71A), providing high input impedance. Indeed, EEG-signals can have a relatively high source impedance due to the electrode interface. This first stage provides amplification of the EEG-signal while removing the common mode component, thus yielding an amplified EEG-signal with enhanced signal to noise ratio. The amplified EEG-signal can be filtered by a filter (71F). The filter (71F) can be a high pass filter configured for removing any remaining DC component of this common mode, mainly due to unequal electrode contacts potentials. The EEG-conditioning circuit can comprise a second stage, including another amplifier (71A) configured for providing further amplification. This can be followed by a low-pass filter (71F).

In some embodiments, it is preferred to transfer an analog EEG-conditioned data. In such cases, it is clear that the analog-to-digital (A/D) converter (71D) is not needed. For example, the amplified and filtered EEG-data can be sent directly through electric wires (36) of the signal transfer lead (60), or can be used to modulate the current fed to a light source (72) in direct optical contact with an optical fibre (31) of the signal transfer lead (60). In another embodiment, the amplified and filtered signal can be modulated in frequency (AL, FM, etc.), by e.g., converting the tension of the amplified and filtered EEG-signal into modulation of frequency (−v to +v signal being transformed into a sine curve of frequency varying between f1 and f2).

In other embodiments, a digitized EEG-signal is sent through the signal transfer lead (60). The amplified and filtered EEG-signal can be digitized in an analog-to-digital (A/D) converter (71D) to yield the digitized EEG-signal to be transferred through the signal transfer lead (60) in the form of electric or optical energy. The digitized EEG-signal can be modulated in frequency, base band, and the like, as well known by a skilled person.

The EEG-conditioning circuit (71C) can also comprise a driver (71V) for modulating as described supra, and/or driving the thus treated EEG-signal through the signal transfer lead (60). The driver (71V) can be configured for supplying enough current to activate a light source (72) in case the signal transfer unit includes an optical fibre (31). The driver (71V) can also convert a 0/1 digitized EEG-signal into a corresponding tension signal, e.g., 0V/5 V, or a current signal, e.g., 0 mA/4 mA).

As described in continuation, the signal transfer lead (60) can comprise one or more electric wires (36) and/or one or more optical fibres (31) for transferring the EEG-conditioned data thus obtained either in the form of electric energy or in the form of optical energy. In case of transferring the EEG-conditioned data in the form of optical energy, the EEG-conditioning circuit also include a light source (72) electrically connected to the last used component of the EEG-conditioning circuit as discussed supra (i.e., either an amplifier (71A), a filter (71F), an A/D-converter (71D), or a driver (71V)). In case of transferring the EEG-conditioned data in the form of electric energy, the EEG-conditioning circuit can comprise an electric socket (73) configured for reversibly coupling a distal end of a conductive wire to the last used component of the EEG-conditioning circuit as discussed supra. Alternatively, the conductive wire (36) of the signal transfer lead (60) can be permanently coupled to the EEG-conditioning circuit.

Signal Transfer Lead (60)

The main function of the signal transfer lead (60) is to transfer the EEG-signal measured by the EEG-electrodes (70a-70d) of the EEG unit (70) to the electronic circuit (53). The EEG-signal can be transferred to the electronic circuit in the form of electric signals through a conductive wire (36), or in the form of optical signals trough an optical fibre (31). The description of the energy transfer unit (30) set forth supra therefore applies mutatis mutandis to the signal transfer lead (60) with the exceptions of, on the one hand, that the distal end is configured for coupling to the EEG-unit (70) instead of the tissue coupling unit (40) and, on the other hand, the proximal end is configured for coupling directly or indirectly to the electronic circuit (53) of the encapsulation unit instead of the IPG (51).

In a first embodiment, wherein the signal transfer unit (60) comprises one or more optical fibres, the EEG-unit (70) comprises an EEG-conditioning circuit (71C), including one or more light sources (72) in optical contact with the one or more optical fibres and configured for emitting a light signal representative of the EEG-signal measured by the EEG-electrodes (70a-70d) and forming the EEG-conditioned data. The encapsulation unit comprises one or more photodetectors in optical communication with the one or more optical fibres of the signal transfer lead, wherein the photodetectors are in communication with the electronic circuit.

In an alternative embodiment, wherein the signal transfer unit (60) comprises one or more conductive wires (36) each comprising a proximal end and a distal end. The distal ends of the one or more conductive wires (36) are coupled in conductive contact with the EEG-electrodes (70a-70d), preferably through the EEG-conditioning circuit (71C), which is configured for yielding the EEG-conditioned data. The EEG-conditioning circuit can comprise an electric socket (73) for reversibly coupling and uncoupling the distal ends of the one or more conductive wires. The proximal ends of the one or more conductive wires (36) are in conductive contact with the electronic circuit (53) of the encapsulation unit.

The signal transfer lead (60) can comprise an optical fibre with a proximal end in optical communication with a light source enclosed in the housing (50h), and with a distal end in optical communication with a photovoltaic cell (71PV) configured for transforming optical energy into electric energy in electrical contact with the EEG-conditioning circuit (71C) for energizing the EEG-conditioning circuit. Alternatively, the signal transfer lead (60) can comprise a conductive wire with a proximal end in electric contact with a power source enclosed in the housing (50h), and with a distal end in electric contact with the EEG-conditioning circuit (71C). These two solutions can be used to supply the energy required for activating and using the EEG-conditioning circuit (71C).

Electronic Circuit (53)

The electronic circuit (53) is enclosed in the housing (50h) of the encapsulation unit (50). It is energized by the battery, preferably the rechargeable battery, also enclosed in the housing (50h), or it is energized by induction by an external source as discussed supra. The electronic circuit controls various functionalities of the AIMD, including sending to the IPG a triggering signal instructing the IPG to trigger energy pulses. In state of the art AIMD's, the electronic circuit is programmed to instruct the IPG to trigger energy pulses according to a predefined pattern independently of the occurrence or not of a seizure, including for example, duration and intensity of individual pulses, as well as frequency and duration of trains of pulses, and intervals between two successive trains of pulses. As discussed in the introduction supra, controlling the IPG according to a predefined pattern independently of the actual occurrence of seizures has the drawbacks of requiring much energy and of favouring the desensitization of the patient to repetitive, often useless stimulations of the vagus nerve.

To overcome the drawbacks of predefined patterns, the electronic circuit of the present invention is configured for
receiving the EEG-conditioned data from the signal transfer lead (60), which is representative of the EEG signal measured by the EEG-unit (70), and
carrying out an analysis of the EEG-conditioned data yielding analysis results, and
optionally storing the EEG-conditioned data or wirelessly transferring the EEG-conditioned data to an external processing unit (90), and
taking a decision based on the analysis results and controlling the IPG according to the decision, wherein the decision includes instructing the IPG to send one or more energy pulses if the analysis results are representative of either a coming seizure, or an incipient or ongoing seizure.

The electronic circuit can comprise an implanted wireless communication device (50c) for transferring the EEG-conditioned data to the external processing unit (90) provided with a corresponding external wireless communication device (90c). For example, the external processing unit can be a smart phone, a smart watch, or smart spectacles of the patient. The implanted wireless communication device can send a signal to the external processing unit (90) when the analysis results are representative of either a coming seizure, or an incipient or ongoing seizure. As shown in FIG. 4(a) the external processing unit, such as a smart phone, can send a warning message to the patient and/or to its treating medical centre. The warning signal can be a vibration, a sound, a light signal, and combinations thereof. The wireless communication can be radio frequency, wifi, Bluetooth, and the like. The external processing unit (90) can for example store the EEG-conditioned data in order to reduce the size of the memory required by the electronic circuit. The entirety of the EEG-conditioned data can be very useful to a medical practitioner for establishing a diagnostic but is not required for the on-demand triggering of the IPG. Consequently, the large memory space required for storing such large volume of information is not necessarily needed in the encapsulation unit and can very well be moved to the external processing unit (90) instead. With the continuous miniaturization of processors, it is, however, preferred to enclose all the computing power in the electronic circuit (53) required for carrying out the analysis of the EEG-conditioned data and for yielding the analysis results.

The EEG-conditioned data is analysed by the electronic circuit (53), to yield the analysis results, which the decision taken by the electronic circuit is based upon. The analysis of the EEG-conditioned data can be carried out by comparing the analysis results with predefined criteria defining the probable imminent occurrence of a seizure or the beginning of a seizure. When such predefined criteria are identified in the EEG-conditioned data, the electronic circuit must instruct the IPG to trigger energy pulses. For example, referring to the EEG represented in FIG. 3, an EEG having a profile according to the period (1) is to be interpreted as corresponding to a normal brain activity and as not representing any sign of an imminent seizure. The profile according to period (3) of FIG. 3 must be clearly interpreted as a seizure, and the analysis should preferably allow triggering a signal before the EEG reaches a profile according to (3). The analysis of the EEG-conditioned data is preferably able to detect a profile according to the period (2) of FIG. 3, which is a transient between period (1) representative of a normal cerebral activity and period (3) representative of a seizure. If such transient period (2) cannot be identified with sufficient certainty, then the predefined criteria must allow triggering energy pulses as early as possible after a profile according to period (3) representative of a seizure is detected. When the predefined criteria representative of a possible seizure are identified in the EEG-conditioned data, the electronic circuit (53) instructs the IPG (51) to send one or more energy pulses.

Alternatively, artificial intelligence (AI) can be implemented in the electronic circuit, wherein through machine learning and big data analytics, the system can "learn" to detect EEG-conditioned data representative of a coming or an incipient seizure with a higher reliability than human clinicians. AI has been extensively used to predict cardiovascular diseases, by identifying abnormal conditions that will lead to patient death, and thus predict the survival rates of patients for the next five years. The prediction accuracy of the next year survival of patients could easily reach 80%, whilst the prediction accuracy of the clinicians was only 60%.

It would be possible to run an algorithm capable of carrying out the foregoing analysis of the EEG-conditioned data by the external processing unit (90), such as a smart phone or a smart watch, and the like, after transfer thereto of the EEG-conditioned data. In the present invention, it is, however, preferred that the analysis be carried out by the electronic circuit (53) to ensure that the analysis is performed continuously at all time, whilst an external processing unit (90), even a smart phone or a smart watch, are not necessarily always within communication distance from the AIMD, and would thus be unable to communicate to the electronic circuit that a seizure is imminent.

Based on the analysis results, the electronic circuit takes a decision. The decision can be to do nothing, as long as the analysis results are representative of a cerebral electrical activity considered as normal, i.e., corresponding to an EEG as illustrated in FIG. 3 representative of a period (1) of normal cerebral activity. By contrast, the decision can be instructing the IPG to send one or more energy pulses as soon as the analysis results are representative of either a coming seizure, or an incipient or ongoing seizure, i.e., corresponding to an EEG as illustrated in FIG. 3 representative of a period (2) or early period (3) a coming or incipient seizure. The decision of instructing the IPG to send one or more energy pulses is preferably taken upon detection in the analysis results of a period (2) EEG, representative of a coming seizure, in order to prevent the occurrence of any seizure.

When the electronic circuit (53) has instructed the IPG to trigger energy pulses, it preferably further instructs the IPG to keep sending pulses until the EEG-conditioned data meets predefined criteria representative of an end of a seizure. In another embodiment of the present invention, the electronic circuit (53) is configured for instructing the IPG (51) to send pulses during a predefined time; and thereafter to stop sending pulses until receiving the next triggering signal from the EEG-unit (70).

AIMD

The AIMD of the present invention comprises the various components described supra, namely,
  a tissue coupling unit (40),
  an EEG-unit (70),
  an encapsulation unit (50) enclosing an IPG (51) and an electronic circuit (53),
  an energy transfer lead (30),
  a signal transfer lead (60).

Depending on the type of energy transfer lead (30) and signal transfer lead (60) used, various combinations of the other components are available.

Chain: IPG (51)—Energy Transfer Lead (30)—Tissue Coupling Unit (40)

In one embodiment, the IPG (51) comprises one or more light sources. The energy transfer lead (30) comprises one or more optical fibres (31) in optical communication with the one or more light sources of the IPG (51). The tissue coupling unit (40) comprises one or more photovoltaic cells (20P) in optical communication with one or more of the optical fibres and in electrical communication with the one or more electrodes (40a, 40b).

A preferred version of this embodiment is a stimulating AIMD defined as follows.

The IPG (51) enclosed in the encapsulation housing comprises the light source(s) which face(s) a window facing the connection device (50x), having a thickness preferably comprised between 300 and 1000 μm and having a transmittance to a wavelength of 850 nm at room temperature of at least 75%. The window separates the inner space from the connection device (50x) and can optionally comprise one or more micro-optical lenses. The connection device (50x) can be integral with a component of the housing (50h).
  The energy transfer lead (30) comprises at least one optical fibre (31), preferably at least two or at least three optical fibres, and no electric wire.
  The proximal end of the optical fibre faces the window and is aligned with at least one of the light sources. The level of alignment between the optical fibre and the light source controls the efficacy of energy transfer from the light source and the optical fibre. A perfect alignment can be obtained with a good connection device (50x), such as described in WO2018068807.

The encapsulation comprises no feedthrough.

The distal end of the optical fibre is connected to the nerve-connection unit (20) of the tissue coupling unit (40), facing a photovoltaic cell (20P) transforming the optical energy transported by the optical fibre into electrical energy transferred to the electrodes (40a, 40b) via the nerve-connection wires (44). Again, a perfect alignment of the optical fibre with the photovoltaic cell (20P) ensures an efficient transfer of energy.

Alternatively, the distal end of the optical fibre is connected to the nerve-connection unit (20) of the tissue coupling unit (40), facing an optrode (80) for guiding a light beam (80B) towards the vagus nerve.

The tissue coupling unit is in the form of a cuff electrode or optrode.

In an alternative embodiment, the IPG comprises an electric IPG (51E) configured for emitting pulses of electric energy and the energy transfer lead (30) comprises one or more electric wires (36) in electrical contact with the electric IPG (51) and with the one or more electrodes (40a, 40b) of the tissue coupling unit.

In a preferred version of the present alternative embodiment, the stimulating AIMD is defined as follows.

The electric IPG (51E) enclosed in the encapsulation housing is in conductive contact with a feedthrough forming the connection device (50x). The feedthrough crosses a wall of the housing and has one end within the inner space, in conductive contact with the IPG (51), and an outer end located outside the housing.

The energy transfer lead (30) comprises at least one conductive wire (36).

The proximal end of the conductive wire (36) is in conductive contact with the outer end of the feedthrough.

The distal end of the conductive wire is connected to the nerve-connection unit (20) of the tissue coupling unit (40), in conductive contact with the nerve-connection wires (44) which are coupled to the electrodes (40a, 40b).

The tissue coupling unit is in the form of a cuff electrode.

An AIMD according to the present invention can of course comprise both conductive wires (36) and optical fibres (31) which can be enclosed in a single or separate protective tubing (35), with corresponding optical and electrical IPG's (51) and photovoltaic cells (20P) facing the optical fibres.

Chain: EEG-Unit (70)—Signal Transfer Lead (60)—Encapsulation Unit (50)

As illustrated in FIGS. 6(a) and 6(b), the EEG-electrodes (70a-70d) of the EEG-unit (70) are in energy transfer contact with the distal end of the signal transfer lead (60), via the EEG-conditioning circuit (71C) configured for conditioning the EEG-signal to yield the EEG-conditioned data. The signal transfer lead (60) can be coupled, preferably reversibly, to the EEG-electrodes via an EEG-connection unit (71). The EEG-connection unit (71) preferably includes the EEG-conditioning circuit (71C) configured for amplifying with an amplifier (71A) the electric signals measured by the EEG-electrodes, preferably followed by other operations such as filtering, digitizing, driving, and the like, the thus amplified signals prior to transferring said signal to the electronic circuit (53) in the encapsulation unit (50) via the signal transfer lead (60). The circuit can be powered from the encapsulation unit (50) through the signal transfer lead (60).

In one embodiment, the signal transfer lead (60) comprises one or more optical fibres (31) for transferring optically the EEG-conditioned data representative of the electric EEG-signals measured by the EEG-electrodes (70a-70d). The EEG-connection unit (71) comprises one or more EEG-light sources (72) such as LED's electrically coupled to the EEG-electrodes (70a-70d) via EEG-connection wires (74) and preferably via the EEG-conditioning circuit (71C) to emit optical signals representative of the electric EEG-signals measured by the EEG-electrodes. When coupled to the EEG-connection unit (71), the one or more optical fibres (31) face in perfect alignment a corresponding EEG-light source (72). The light emitted by the one or more EEG-light sources is transferred through the one or more optical fibres (31) of the signal transfer lead (60) to corresponding photodetectors located in the inner volume of the encapsulation unit (50). The EEG-conditioned data thus received is transferred from the photodetectors to the electronic circuit (53) where it is processed as discussed supra, to determine the analysis results and take a decision depending on whether the analyse results conclude on a coming or incipient seizure, prompting or not the IPG to trigger energy pulses to stimulate the vagus nerve.

In an alternative embodiment, the signal transfer lead (60) comprises one or more conductive wires (36) for conducting the electric signals measured by the EEG-electrodes (70a-70d). The EEG-connection unit (71) can comprise an electric socket (73) electrically coupled to the EEG-electrodes (70a-70d), configured for reversibly coupling the one or more conductive wires (36) to the EEG-connection wires (74), preferably via the EEG-conditioning circuit (71C), to conduct the electric signals measured by the EEG-electrodes to the electronic circuit (53). Alternatively, the one or more conductive wires (36) can be permanently connected to the EEG-connection unit (71), either directly to a corresponding EEG-electrode (70a-70d) or via the EEG-conditioning circuit. In this embodiment, the signal transfer lead (60) cannot be separated from the EEG-unit (70).

In a first embodiment of the EEG-unit comprising a circuit to be powered from the encapsulation unit (50), the signal transfer lead (60) can comprise an optical fibre (31) comprising, a proximal end coupled to one of the one or more connection devices (50x) of the encapsulation unit, facing in optical communication through a window a source of light energy enclosed in the housing (50h), and p1 a distal end coupled to the EEG-connection unit (71), facing in optical communication a photovoltaic cell for transforming optical energy into electric energy for powering the EEG-unit.

In a second embodiment, the signal transfer lead (60) can comprise an additional conductive wire (36) comprising, a proximal end coupled to one of the one or more connection devices (50x) of the encapsulation unit, in electric contact with a source of electric energy enclosed in the housing (50h), and a distal end coupled to the EEG-connection unit (71), for powering the EEG-unit.

On-Demand Neurostimulation

An AIMD according to the present invention as described supra permits to stimulate a nerve, such as the vagus nerve only when required to prevent a coming seizure or stop short an incipient seizure. The on-demand stimulation of the vagus nerve has enormous advantages over conventional neurostimulators which are programmed for stimulating the vagus nerve with energy pulses at regular intervals, regardless of whether stimulation is required or not. It saves energy, which increases the comfort of the patient who can live longer between two consecutive loading operations, and it decreases the phenomenon of habituation, which leads to a desensitization of the vagus nerve and/or neural system to the energy stimulations. Such habituation requires the intensity and frequency of stimulation to be increased, which leads to a further habituation and so on, forming a vicious cycle. The discussion is based on the stimulation of the vagus nerve, but it is clear that it can apply to any nerve whose stimulation can prevent or stop short a seizure.

The EEG-electrodes (70a-70d) monitor continuously or intermittently the electric activity of selected areas of the brain of a patient. The information is conveyed to the electronic circuit (53) enclosed in the encapsulation unit (50) in the form of EEG-conditioned data after conditioning by the EEG-conditioning circuit (71C) of the EEG-signal measured by the EEG-electrodes (50a-70d). The electronic circuit (63) analyses the EEG-conditioned data to generate analysis results. As long as the analysis results are representative of a "normal" cerebral electro-activity, the electronic circuit does not instruct the IPG to trigger any energy pulse. As soon as the analysis results are representative of a coming or incipient seizure, the electronic circuit (53) instructs the IPG (51) to immediately trigger energy pulses to stimulate the vagus nerve (VN) and prevent or abort the upcoming seizure. The electronic circuit can instruct the IPG to send energy pulses for a predetermined period of time. In a preferred embodiment, the electronic circuit instructs the IPG to send energy pulses as long as the analysis results are not representative of an end of the seizure, thus forming a closed loop control system. This decision making by the electronic circuit based on instantaneous live data measured in situ is a major breakthrough in the field of neurostimulation. In case the EEG-electrodes measure the brain activity only intermittently, at a first frequency of measurements, the electronic circuit (53) can instruct the EEG-unit to increase the frequency of measurements to a second frequency higher than the first frequency, while the IPG is sending energy pulses, so as to have a finer time analysis of the evolution of a seizure, and to instruct the IPG to keep or stop sending energy pulses more synchronously with the evolution of the seizure The AIMD of the present invention is little invasive. It must, of course, be implanted in a body of a patient, but the implantation of the encapsulation unit (50) and of the tissue coupling unit (40) is a relatively easy operation and, in particular, the subcutaneous implantation of the EEG-unit can be quite easy compared with epidural implantation, and brain implantation, over or through the dura matter, in an increasingly invasive order. Brain electrodes and in particular, intra-cerebral electrodes are preferably avoided unless imposed by the treatment.

| REF# | Feature |
| --- | --- |
| 1 | Period of normal cerebral activity in EEG |
| 2 | Transition period between normal activity and seizure in EEG |
| 3 | Period of seizure in EEG |
| 4 | Recovery period in EEG |
| 20 | nerve-connection unit btw energy transfer lead and tissue coupling unit |
| 20P | Photovoltaic cell |
| 30 | Energy transfer lead |
| 31 | Optical fibre |
| 32 | Optical fibre cladding |
| 33 | Optical fibre core |
| 35 | Protective tubing |
| 36 | Conductive wire |
| 40 | Tissue coupling unit |
| 40a, 40b | Electrode |

-continued

| REF# | Feature |
| --- | --- |
| 43 | Insulating support sheet |
| 44 | nerve-connection wire |
| 50 | Encapsulation |
| 50c | Wireless communication device of the encapsulation |
| 50h | Housing |
| 50x | Connection device to encapsulation unit |
| 51 | IPG |
| 51E | Electric pulse generator |
| 51L | IPG light source |
| 53 | Electronic circuit |
| 60 | Signal transfer lead |
| 64 | Connection lead |
| 70 | EEG-unit |
| 70a-70d | EEG-electrodes |
| 71 | EEG-connection unit btw energy transfer lead and EEG-unit |
| 71A | Amplifier of EEG-conditioning circuit |
| 71C | EEG-conditioning circuit |
| 71D | Analog-to-digital converter of EEG-conditioning circuit |
| 71F | Filter of EEG-conditioning circuit |
| 71PV | Photovoltaic cell of EEG-conditioning circuit |
| 71V | Driver |
| 72 | EEG light source of EEG-conditioning circuit |
| 73 | Electric socket of EEG-conditioning circuit |
| 74 | EEG connection wire |
| 75 | EEG-support |
| 80 | Optrode |
| 80B | Light beam |
| 80S | Light sensing unit |
| 90 | External processing unit |
| 90c | Wireless communication device of the external processing unit |
| t1 | End of period of normal activity (1) |
| t2 | End of transition period (2) |
| t3 | End of period of seizure (3) |
| Vn | Vagus nerve |

The invention claimed is:

1. An implantable stimulating device (10) for electrically or optically stimulating a vagus nerve (Vn), comprising,
   (a) a tissue coupling unit (40) comprising one or more electrodes (40a, 40b) or optrodes configured for being implanted directly onto the vagus nerve (Vn) of a patient to stimulate the vagus nerve with voltages of 15V±5V,
   (b) an EEG-unit (70) comprising EEG-electrodes (70a-70d) and configured for measuring an electroencephalogram (EEG-) signal of the patient,
   (c) an encapsulation unit (50) configured for being subcutaneously implanted in the patient body, and comprising a housing (50h) enclosing,
       an implanted pulse generator (IPG) (51) configured for emitting pulses of optical energy,
       an electronic circuit (53) configured for sending a triggering signal to the IPG (51) instructing the IPG to trigger energy pulses,
   (d) an energy transfer lead (30) configured for transferring pulses of optical energy between the IPG and the tissue coupling unit, and comprising
       a proximal end configured for coupling to the encapsulation unit and
       a distal end configured for coupling to the tissue coupling unit,
   (e) a signal transfer lead (60) configured for transferring signals between the EEG-unit and the electronic circuit, and comprising
       a proximal end configured for coupling to the encapsulation unit and
       a distal end configured for coupling to the EEG-unit, wherein the electronic circuit is configured for, receiving EEG-conditioned data from the signal transfer lead (60), which is representative of the EEG signal measured by the EEG-unit (70), and carrying out an analysis of the EEG-conditioned data yielding analysis results and taking a decision based on the analysis results and controlling the IPG according to the decision, wherein the decision includes instructing the IPG to send one or more energy pulses if the analysis results are representative of either a coming seizure, or an incipient or ongoing seizure, characterized in that, the energy transfer lead (30) comprises one or more optical fibres, and in that the signal transfer lead (60) consists of one or more optical fibres.

2. The implantable stimulating device according to claim 1, wherein controlling the IPG includes after instructing the IPG to send one or more pulses, to instruct the IPG to keep sending pulses either, until the analysis results become indicative of an end of a seizure, or for a predetermined duration in time, and thereafter to stop sending pulses until the analysis results are again representative of either a coming seizure, or an incipient or ongoing seizure.

3. The implantable stimulating device according to claim 1, wherein, the IPG (51) comprises one or more light sources (51L), the energy transfer lead (30) comprises one or more optical fibres in optical communication with the one or more light sources of the IPG, and the tissue coupling unit (40) comprises one or more photovoltaic cells (20A) in optical communication with one or more of the optical fibres and in electrical communication with the one or more electrodes (40a, 40b).

4. The implantable stimulating device according to claim 3, wherein the energy transfer lead (30) is devoid of an electric wire.

5. The implantable stimulating device according to claim 4, wherein a signal transfer lead (60) is devoid of an electric wire.

6. The implantable stimulating device according to claim 1, wherein, the EEG-unit (70) comprises an EEG-conditioning circuit (71C) configured for conditioning the EEG-signal to yield the EEG-conditioned data, the EEG-conditioning circuit comprising one or more light sources (72) configured for emitting a light signal representative of the EEG-signal measured by the EEG-electrodes (70a-70d) and forming the EEG-conditioned data, the signal transfer lead (60) comprises one or more optical fibres in optical communication with one or more light sources (72) of the EEG-conditioning circuit (71C), and the encapsulation unit comprises one or more photodetectors in optical communication with the one or more optical fibres of the signal transfer lead, the photodetectors being in communication with the electronic circuit.

7. The implantable stimulating device according to claim 6, wherein the EEG-conditioning circuit (71C) comprises one or more amplifiers (71A) to yield an amplified EEG-signal.

8. The implantable stimulating device according to claim 7, wherein the EEG-conditioning circuit (71C) comprises one or more of the following elements:

filters (71F) for filtering the amplified EEG-signal and yielding a filtered EEG-signal, an analog-to-digital (A/D) converter (71D) for digitizing the amplified EEG-signal or the filtered EEG-signal to yield a digitized EEG-signal, an encoding and signal compressing and multiplexing logic to reduce size of the data to be transmitted, and a driver (71V) for modulating and/or driving the thus treated EEG-signal through the signal transfer lead (60).

9. The implantable stimulating device according to claim 7, wherein the signal transfer lead (60) comprises an optical fibre with a proximal end in optical communication with a light source enclosed in the housing (50h), and with a distal end in optical communication with a photovoltaic cell (71PV) configured for transforming optical energy into electric energy in electrical contact with the EEG-conditioning circuit (71C) for energizing the EEG-conditioning circuit.

10. The implantable stimulating device according to claim 1, wherein the EEG-electrodes (70a-70d) of the EEG-unit are configured for measuring the electrical activity of an area of the brain and are_selected among one or more of, subcutaneous electrodes configured for being implanted subcutaneously over the skull, preferably attached to the skull, or epidural electrodes configured for being implanted epidurally, namely under the skull and over the dura mater, or brain electrodes configured for being implanted below the dura matter and directly over the brain surface, or intra-cerebral electrodes, configured for being implanted within the brain.

11. The implantable stimulating device according to claim 1, wherein the encapsulation (50) comprises no battery, and comprises a coil for inducing an electric current upon exposure to a magnetic field from an external source of energy.

12. The implantable stimulating device according to claim 1, wherein the encapsulation encloses a battery for energizing the implantable stimulating device.

13. The implantable stimulating device according to claim 12, wherein the battery is a rechargeable battery.

* * * * *